United States Patent [19]

Henry et al.

[11] Patent Number: 5,868,756
[45] Date of Patent: Feb. 9, 1999

[54] HANDPIECE FOR USE IN LITHOTRIPSY

[75] Inventors: Nicole Henry, Burtigny, Switzerland; Roberto Hassan, Milano, Italy

[73] Assignee: Ferton Holding, Delemont, Switzerland

[21] Appl. No.: 846,690

[22] Filed: Apr. 30, 1997

[30] Foreign Application Priority Data

May 10, 1996 [DE] Germany ................. 196 18 972.1

[51] Int. Cl.⁶ ..................................................... A61B 17/22
[52] U.S. Cl. ............................................................ 606/128
[58] Field of Search ..................................... 606/128, 169

[56] References Cited

U.S. PATENT DOCUMENTS

| | | |
|---|---|---|
| 2,542,695 | 2/1951 | Neff et al. . |
| 5,160,336 | 11/1992 | Favre ........................ 606/128 |
| 5,176,688 | 1/1993 | Narayan et al. . |
| 5,449,363 | 9/1995 | Brust et al. . |
| 5,540,702 | 7/1996 | Walz . |

FOREIGN PATENT DOCUMENTS

| | | |
|---|---|---|
| 317507 | 4/1992 | European Pat. Off. . |
| 4405656 | 8/1995 | Germany . |
| 2161079 | 1/1986 | United Kingdom . |
| 2277450 | 11/1994 | United Kingdom . |

*Primary Examiner*—Michael H. Thaler
*Attorney, Agent, or Firm*—Ratner & Prestia

[57] ABSTRACT

A handpiece for use in lithotripsy is provided with a probe which as a wave guide transmits shock waves that are produced by an impact force of a projectile acting against a mass body member located at the proximal end of the probe whereby this mass body member is located at the free end of a guide tube for said projectile and adapted for transmitting the impact force from the projectile to said probe the shock waves of which are adapted to cause an intercorporeal fragmentation of calculi.

18 Claims, 1 Drawing Sheet

HANDPIECE FOR USE IN LITHOTRIPSY

TECHNICAL FIELD

The present invention relates to a handpiece for use in lithotripsy and more particularly to a handpiece in a combination with an intracorporeal lithotripter of the kind as disclosed in U.S. Pat. No. 5,160,336 which is adapted to effect an intracorporeal fragmentation of calculi such as nephroliths, ureteroliths or urinary calculi by using an endoscope.

BACKGROUND ART

U.S. Pat. No. 5,160,336 discloses a lithotripter having a handpiece which is adapted for holding a probe. The probe forms a waveguide which is adapted to transmit impact energy that is produced by a projectile. The projectile is pneumatically driven within a guide tube for periodically causing an impact force against the proximal end of the probe to thereby obtain shock waves at the distal end of the probe.

The probe is adapted for being inserted into an endoscope. Different sizes and diameters of the probe are provided for being used in an exchangeable manner under particular consideration of any specifically intended intracorporeal fragmentation of calculi. The holding means for the exchangeable probes as provided on the handpiece are generally designed as a screw cap having a seat for the proximal end of a probe whereby the proximal end of the probe has an enlarged head portion serving with its proximal face as an impact area for the projectile.

The screw cap further comprises a throughhole beyond which the distal end of the probe projects for its insertion into an endoscope. The screw cap has a male thread in engagement with a female thread on a cylindrical casing and sealed by means of an O-ring seal which is arranged on the screw cap. The screw cap thusly allows an easy exchange of the probes. The particular design of the holding means further allows a sterilization of the probes separate from the handpiece. Any sterilization of the handpiece necessitates, however, that after the removal of the screw cap the hollow of the casing in which the projectile is housed and which is then open to the air must first be closed by a separate sealing cap. By such closing also loss of the projectile during the sterilization of the handpiece will be prevented. The separate sealing cap finally also prevents any contamination of the projectile and of its guideway in the guidetube.

STATEMENT OF THE INVENTION & ADVANTAGES

The principal object of the present invention is to provide an improved handpiece for use in lithotripsy which primarily prevents any risk for contamination of the hollow that houses the projectile during any exchange of the probe.

Another object of the present invention is to provide a handpiece of this type that will allow a separate sterilization of the probes and of the handpiece without necessitating before a sealing of the hollow that houses the projectile when the handpiece will be sterilized so that when a probe will again be mounted on the handpiece after its sterilization the handpiece will then be ready for an immediate take-up of the drive for the projectile.

These and other objects are achieved by a handpiece of the more general design as above referred to and incorporating additionally in accordance with the present invention an additional mass body member which is inserted into the distal end of the guide tube for the projectile in a sealed manner whereby this additional mass body member is more generally also adapted to transmit the impact forces from the projectile to the probe whenever the projectile hits against the proximal face of the additional mass body member.

By the arrangement of such an additional mass body member as adapted for transmitting impact forces no disadvantages will be obtained in respect to the creation of the shock waves at the distal end of the probe as long as the mass and the material of such an additional mass body member will be conveniently chosen in relation to those of the projectile. The shock waves in this case result as well from the impact energy as created by the impact forces of the projectile.

Such an additional mass body member namely follows the Newton's axioms according to which any body remains in its rest position or in its uniform rectilinear motion respectively as long as no forces are acting on the body. The additional mass body member which in accordance with the present invention is inserted into the guide tube for guiding the projectile therefore serves as an ideal sealing body since it remains stationary at the moment of an impact of the projectile against the proximal face of the same. The impact force which is created by the projectile will accordingly be transmitted to the probe via the additional mass body member in accordance with the principle of reaction in the same manner as in case of an impact of the projectile directly against the probe.

DRAWING

The foregoing described embodiment of a handpiece in accordance with the present invention as well as other aspects and features of the same as described and defined in the appended claims will be better understood by reference to the following description of the drawing. The drawing is a cross sectional view in an enlarged scale only of the tip end of a handpiece for use in lithotripsy and showing the means for fixation of a probe at the location of the mass body member which is hit by a pneumatically driven projectile for causing an impact force at an interface thereof.

DETAILED DESCRIPTION OF THE DRAWING

Figure 1:
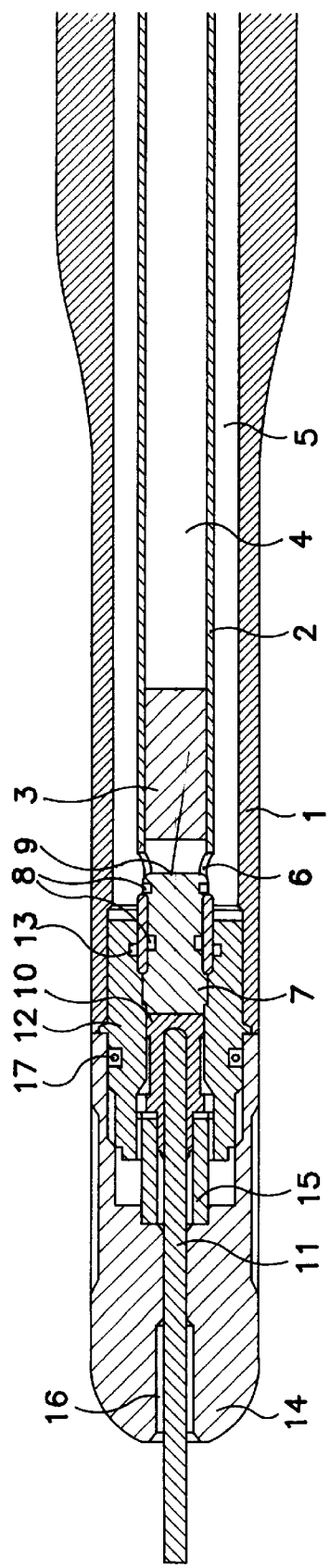

Referring to the drawing, a tip end of a handpiece for use in lithotripsy in accordance with the present invention is shown. This handpiece basically achieves the same function and operates in the same manner as a handpiece of a lithotripter of the kind as described in U.S. Pat. No. 5,160,336. The disclosure of this document is therefore incorporated herein for any supplemental reference to its particular operation in achieving the intracorporeal fragmentation of calculi with the use of an endoscope.

The handpiece is provided with a cylindrical casing 1 for coaxially housing a guide tube 2. In this guide tube 2 a projectile 3 is arranged which is pneumatically driven for being moved in a reciprocating manner. The respective pneumatic drive acts between the inner hollow 4 of the guide tube 2 and a surrounding annular space 5 which communicates with the hollow 4 at the distal end of the guide tube 2 through apertures 6 controlling the flow rate of the air therebetween. Further details of this particular pneumatic drive may be derived from the above referred U.S. Pat. No. 5,160,336. Instead of a pneumatic drive also a hydraulic or an electromagnetic drive could be used for the projectile.

Into the distal end of the guide tube 2 a mass body member 7 is tightly inserted and sealed by two O-ring seals 8. This particular mass body member 7 is provided with a mass that substantially corresponds with that of the projectile 3.

It is further composed of the same material as the projectile. When the projectile 3 hits against this mass body member 7 when being driven forwardly an impact force will be created on a proximal impact face 9 of the mass body member 7.

This impact force will then be transmitted to an enlarged head 10 at the proximal end of a probe 11 to thereby create shock waves at the distal end of the probe 11 as a result of the impact energy which is derived from the impact force. These shock waves will then be used at the distal end of the probe for an intracorporeal fragmentation of calculi. The transmission of the impact force takes place in the same manner as if the projectile 3 would directly hit the proximal end of the probe 11 since the mass body member 7 remains at its rest position when being hit by the projectile. In accordance with the Newton's axioms and the respective reaction principle the impact force is directly transmitted to the probe 11. Since the mass body member 7 remains at a rest position when being hit by the projectile, it provides at the same time an optimum sealing action for the distal end of the guide tube 2.

A further sealing action of the mass body member 7 is obtained by means of a guide bush 12 which is provided with a male thread which is engaged by a female thread of the casing 1. This guide bush 12 has a sliding seat on the distal end of the guide tube 2 against which it is sealed by a further O-ring seal 13. The guide bush 12 surrounds the projecting end of the mass body member 7 as well as the proximal end of the probe 11 at its enlarged head 10 being directly in contact with the mass body member 7.

The guide bush 12 is engaged by a screw cap 14 by means of complementary male and female threads. The screw cap 14 forms a seat for a silicone packing 15 which surrounds the proximal end of the probe 11. It is further provided with a throughhole 16 through which the proximal end portion of the probe 11 extends whereas its remaining main length extends forwardly of the screw cap 14 for being inserted into an endoscope (not shown). The screw cap 14 is sealed on the guide bush 12 by means of an O-ring seal 17. A corresponding seal (not shown) of the guide bush 12 is also provided in relation to the casing 1.

When the screw cap 14 is removed from the guide bush 12 along the projecting length of the probe then the probe 11 may be grasped and pulled out from its seat in the guide busch 12. The probe 11 may then be sterilized separately from the handpiece. For a sterilization of the handpiece the mass body member 7 on the other side keeps the distal end of the guide tube 2 sealed and also the distal end of the casing 1 by means of its engagement with the guide bush 12. The entire drive unit for the projectile 3 therefore remains closed. No contamination of the drive unit will occur during sterilization and any loss of the projectile 3 will be prevented by the mass body member 7 when the screw cap 14 is removed.

The mass and/or the material of the mass body member could be conveniently chosen such as to be different from the projectile. Any arbitrary influence on the impact forces as obtained by the projectile and transmitted by the mass body member would thusly be achieved so that the shock waves resulting from such different impact forces and obtained at the distal end of the probe would be applicable in accordance with any specific medical intentions. Such a mass body member will also allow the realization of a transmission path of the impact force from the projectile to the probe different from the one as herein described.

The functional principle of the mass body member to act as a sealing member and at the same time as a transmission member for impact forces may not only be used in the field of lithotripsy but may also be used in the field of orthopedics where use is made of such impact forces as well and which then will be transmitted by the inclusion of such an additional mass body member. As regards the particular transmission of the impact forces it is further most important that the mass body member always remains in a rest position so that the proximal end of the probe is kept resistant to wear. This is not the case where the projectile directly hits against the proximal face of the probe.

The advantages of the mass body member could be realized for different drive systems for the projectile. The design of the mass body member and the design of the projectile are only of a secondary significance as long as an undisturbed transmission of the impact energy to the probe will be achieved.

We claim:

1. Handpiece for use in lithotripsy, comprising
    a probe being provided as a wave guide for transmission of an impact energy which produces shock waves, said probe being dimensioned such as to be inserted into an endoscope;
    b. a projectile which is arranged inside of a guide tube of said handpiece and driven in a reciprocating manner, said projectile being arranged for producing an impact force against a separate mass body member having a first end adapted to receive said impact force from said projectile, and a second end juxtaposed to and in direct contact with a proximal end of said probe whereby impact force on said mass body member is transmitted to said proximal end of said probe;
    c. a guide bush sealingly engaged to said guide tube and a casing of said handpiece surrounding said guide tube, said guide bush being adapted for removeably holding said probe at its proximal end;
    d. said mass body member being inserted in a sealed manner into a distal end of said guide tube; and
    e. a removable cap adapted to removeably and sealingly engage said guide bush while permitting said probe to extend outwardly therefrom.

2. Handpiece according to claim 1, wherein said mass body member has approximately the same mass as said projectile.

3. Handpiece according to claim 1, wherein said mass body member has a different mass than said projectile.

4. Handpiece according to claim 1, wherein the mass of said mass body member is greater than the mass of said projectile.

5. Handpiece according to claim 1, wherein the mass of said mass body member is smaller than the mass of said projectile.

6. Handpiece according to claim 1, wherein said mass body member is of the same material as said projectile.

7. Handpiece according to claim 1, wherein said mass body member is substantially cylindrical and is sealed against said guide tube by at least one O-ring seal.

8. Handpiece according to claim 1 wherein said guide bush has a sliding seat on the distal end of the guide tube against which it is sealed.

9. Handpiece according to claim 1, wherein said guide bush is screwed to said casing by means of cooperating male and female threads.

10. A handpiece for use in lithotripsy, comprising
    a. a probe being provided as a waveguide for transmission of an impact energy which produces shock waves, said probe being dimensioned so as to be inserted into an endoscope;

b. a projectile which is arranged inside of a guide tube of said handpiece and driven in a reciprocating manner, said projectile being arranged for producing an impact force against a separate mass body member juxtaposed to a proximal end of said probe;

c. a holding means sealingly engaged to said guide tube and a casing of said handpiece surrounding said guide tube, said holding means being adapted for removeably holding said proximal end of said probe, said proximal end of said probe inserted into a guide bush acting as said holding means, said guide bush having a sliding seat on the distal end of said guide tube against which it is sealed; and d. said mass body member being inserted in a sealed manner into a distal end of said guide tube, said mass body member being adapted to transmit the impact force of the projectile to said proximal end of the probe when the projectile hits against the mass body member on a face opposite to the proximal end of the probe.

11. A handpiece according to claim 10, wherein said guide bush is screwed to said casing by means of cooperating male and female threads.

12. A handpiece according to claim 10, wherein said holding means includes a screw cap which forms a seat for said proximal end of said probe, said screw cap being provided with a through hole, said screw cap being fastened to said guide bush by means of cooperating male and female threads.

13. A handpiece according to claim 10, wherein said mass body member has approximately the same mass as said projectile.

14. A handpiece according to claim 10, wherein said mass body member has a different mass than said projectile.

15. A handpiece according to claim 10, wherein the mass of said mass body member is greater than the mass of said projectile.

16. A handpiece according to claim 10, wherein the mass of said mass body member is smaller than the mass of said projectile.

17. A handpiece according to claim 10, wherein said mass body member is of the same material as said projectile.

18. A handpiece according to claim 10, wherein said mass body member is substantially cylindrical and is sealed against said guide tube by at least one O-ring seal.

* * * * *